United States Patent
Howell et al.

(10) Patent No.: US 6,989,017 B2
(45) Date of Patent: *Jan. 24, 2006

(54) SURGICAL CLAMP PAD WITH INTERDIGITATING TEETH

(75) Inventors: Thomas A. Howell, Palo Alto, CA (US); Douglas S. Sutton, Pacifica, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 366 days.

This patent is subject to a terminal disclaimer.

(21) Appl. No.: 10/133,511

(22) Filed: Apr. 25, 2002

(65) Prior Publication Data

US 2002/0183785 A1 Dec. 5, 2002

Related U.S. Application Data

(63) Continuation of application No. 09/578,626, filed on May 25, 2000, now Pat. No. 6,387,106, which is a continuation of application No. 09/122,836, filed on Jul. 27, 1998, now Pat. No. 6,099,539.

(51) Int. Cl.
 *A61B 17/08* (2006.01)

(52) U.S. Cl. ........................................ 606/151; 606/207
(58) Field of Classification Search .............. 606/151, 606/157, 158, 205–209, 142, 139
See application file for complete search history.

(56) References Cited

U.S. PATENT DOCUMENTS

| | | |
|---|---|---|
| 2,743,726 A | 5/1956 | Grieshhaber |
| 3,503,396 A | 3/1970 | Pierie et al. |
| 3,503,397 A | 3/1970 | Fogarty et al. |
| 3,503,398 A | 3/1970 | Fogarty et al. |
| 3,515,139 A | 6/1970 | Mallina |
| 3,746,002 A | 7/1973 | Haller |
| 3,880,166 A | 4/1975 | Fogarty |
| 3,993,076 A | 11/1976 | Fogarty |
| 4,548,202 A | 10/1985 | Duncan |
| 4,611,593 A | 9/1986 | Fogarty et al. |
| 4,821,719 A * | 4/1989 | Fogarty ................... 606/158 |
| 5,171,253 A | 12/1992 | Klieman |
| 5,242,458 A * | 9/1993 | Bendel et al. ............. 606/205 |
| 5,258,005 A | 11/1993 | Christian |
| 5,535,756 A | 7/1996 | Parasher |
| 5,674,220 A | 10/1997 | Fox et al. |
| 5,722,982 A | 3/1998 | Ferreira et al. |

FOREIGN PATENT DOCUMENTS

| | | |
|---|---|---|
| EP | 0 490 301 A1 | 12/1991 |
| WO | WO 98/33437 | 8/1998 |

* cited by examiner

*Primary Examiner*—Kevin T. Truong
(74) *Attorney, Agent, or Firm*—Morrison & Foerster LLP

(57) ABSTRACT

Opposable surgical clamp members having opposable resilient pads with wedge-shaped and cylindrical protrusions extending from the surfaces of the pads and the use of such members for occluding vessels and other tubular body structures are described. The protrusions are arranged such that when the members are moved toward one another, the protrusions of one pad interdigitate with the protrusions of the other pad. Upon engagement with a vessel, portions of the vessel are forced into the interdigital spaces providing for improved gripping of the vessel. The protrusions also resist lateral or transverse movement of a clamped vessel relative to the pads. The existence of through holes under the pad surface alters the relative resiliency of the pad, allowing for an overall pad resiliency that minimizes trauma to a clamped vessel while allowing the local resiliency of the protrusions themselves to be of a hardness to avoid excessive deflection and retain the desired shape and gripping ability.

5 Claims, 5 Drawing Sheets

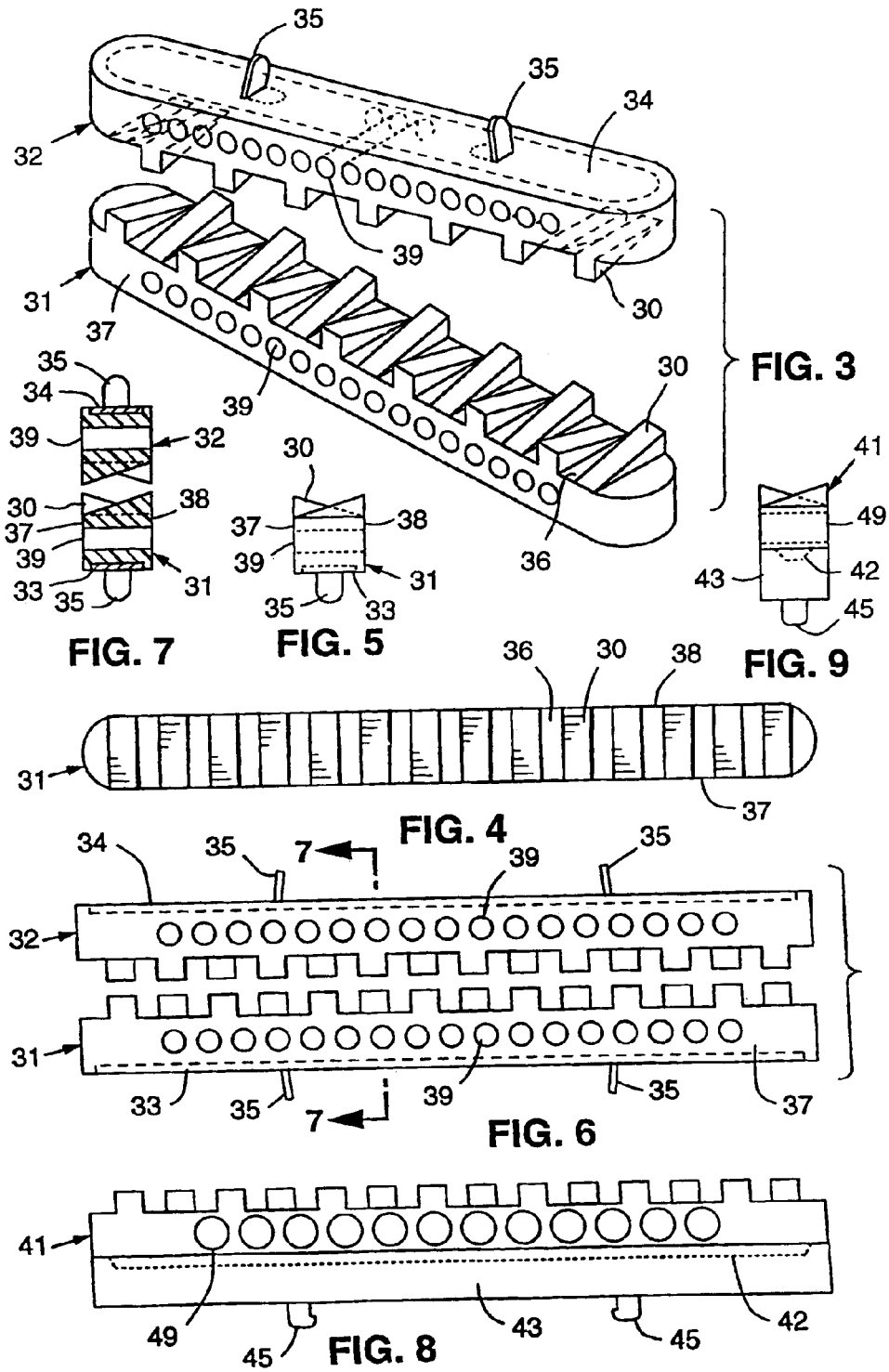

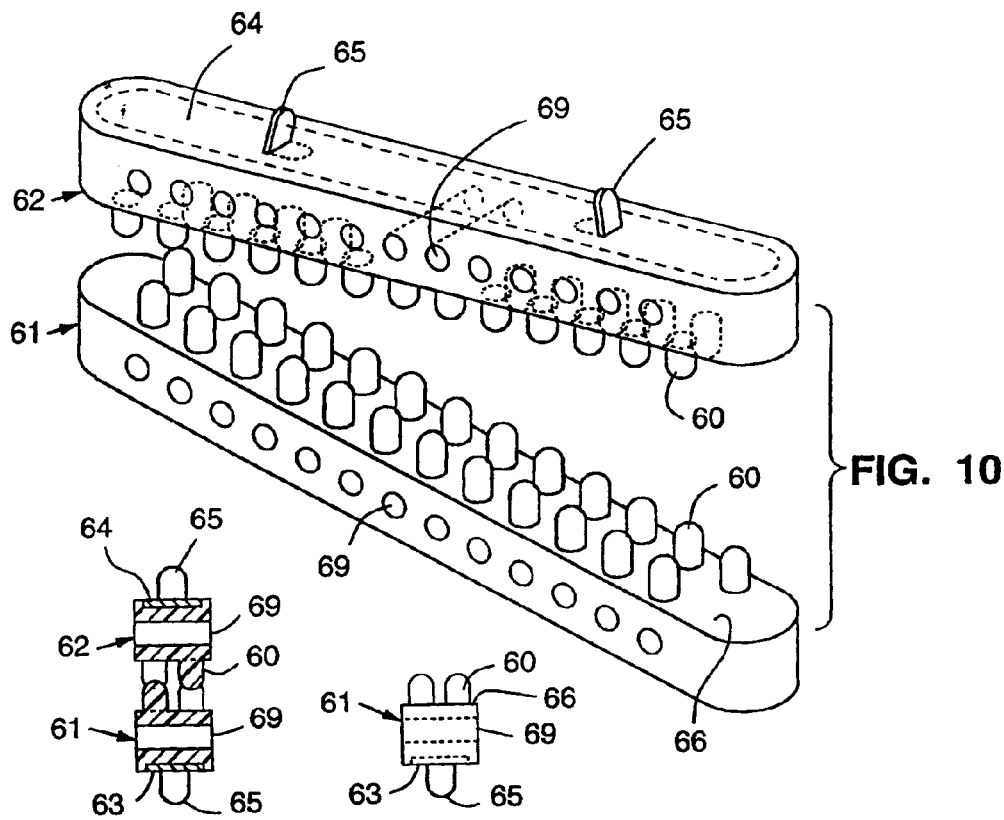
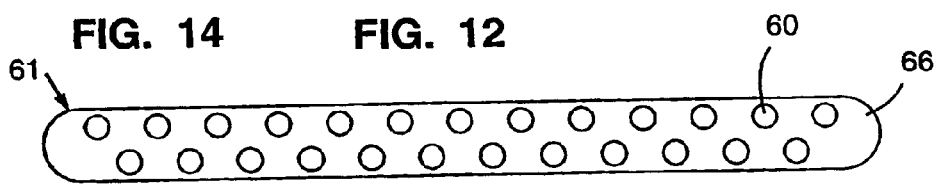
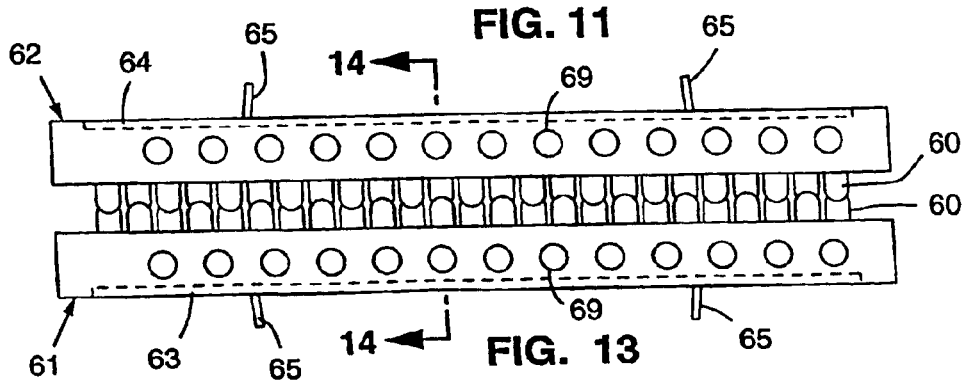

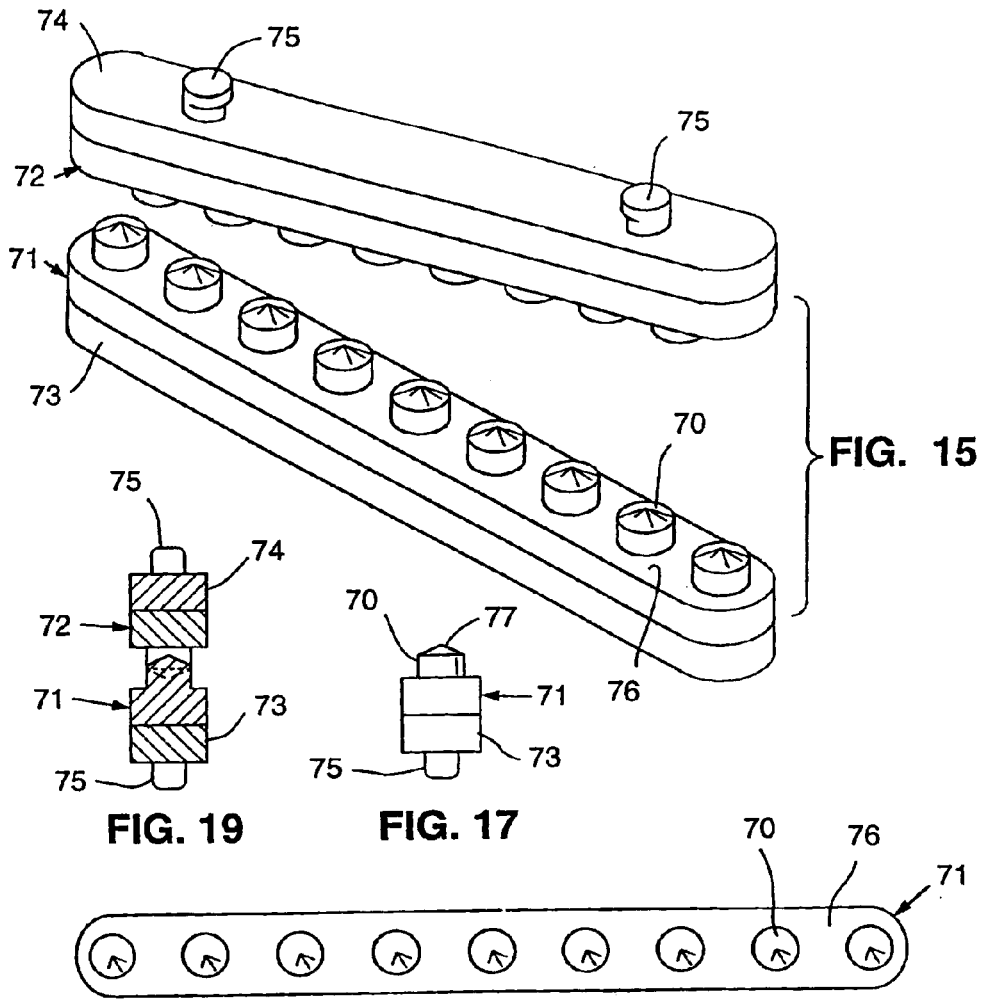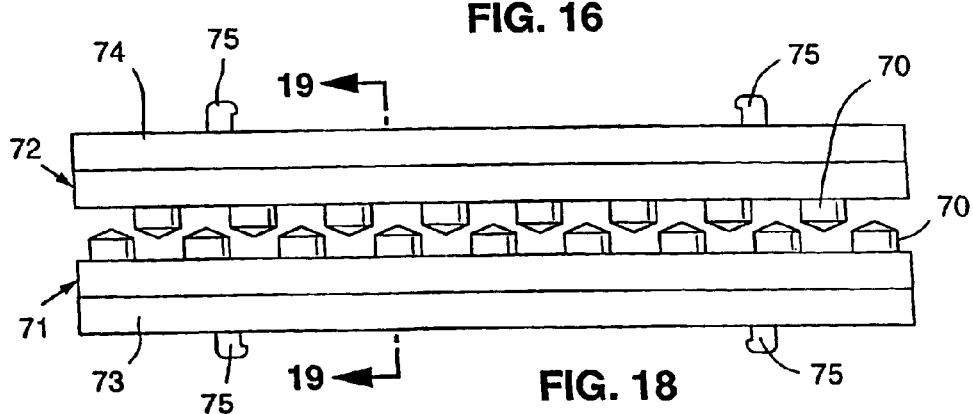

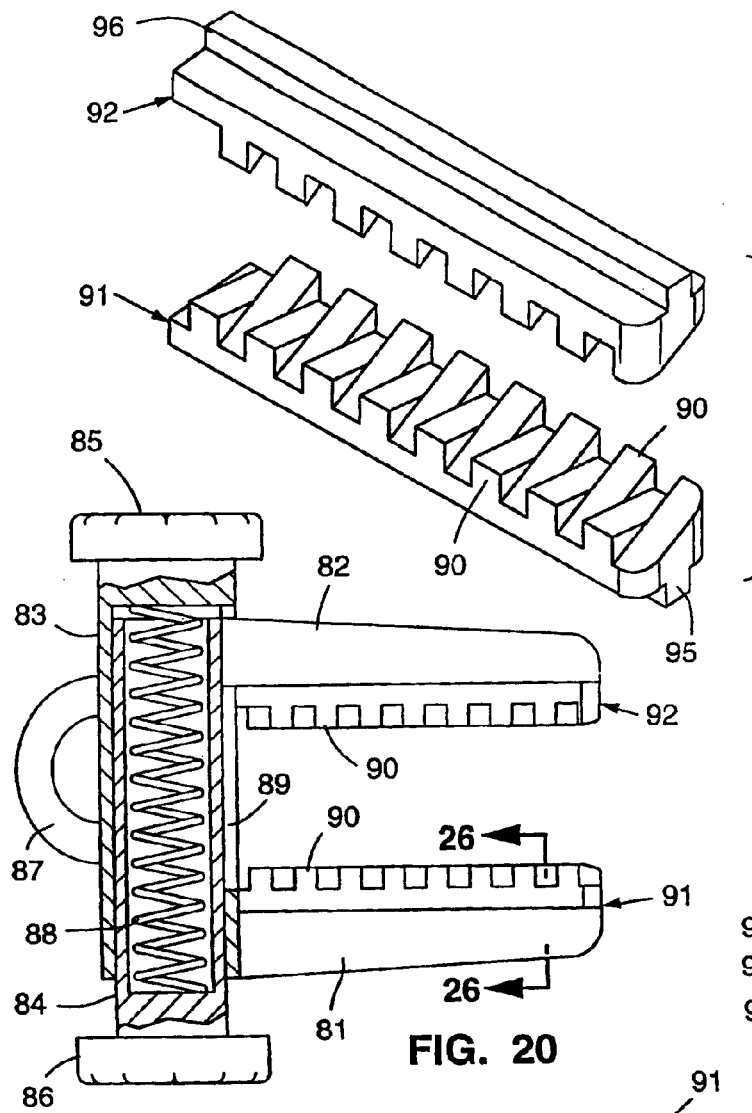
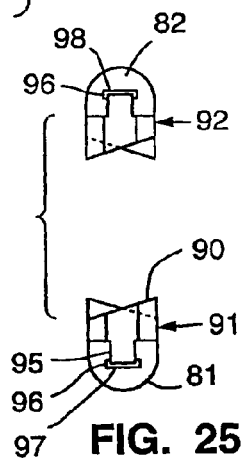
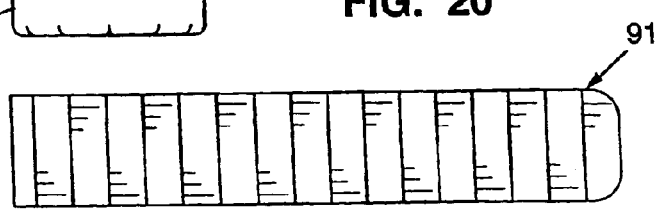
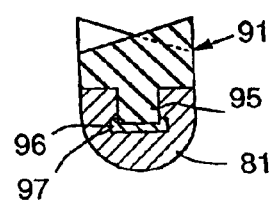
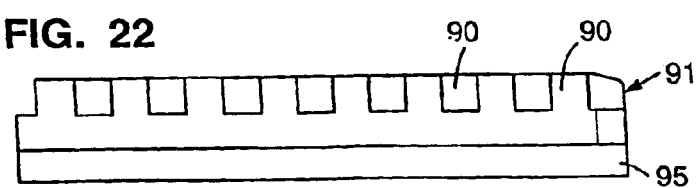
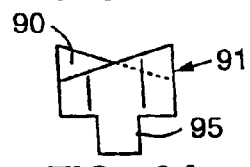

SURGICAL CLAMP PAD WITH INTERDIGITATING TEETH

BACKGROUND OF THE INVENTION

1. Field of the Invention

The present invention relates generally to clamping members for attachment to a jaw-type surgical clamping device for atraumatically occluding a vessel or other tubular structure. More particularly, the invention relates to clamping members that include opposable resilient pads having surface protrusions where the protrusions of the opposing pads interdigitate to provide improved gripping of the occluded vessel or tubular structure.

2. Description of the Related Art

Instruments for occluding blood vessels or other tubular structures of a patient's body during surgery, such as conventional metal or rigid surgical clamps or clips, are well known. Such instruments, however, are known to cause trauma to the clamped vessel at the clamping site. A number of atraumatic instruments have been developed for reducing or eliminating the trauma to a vessel during occlusion of the vessel. U.S. Pat. No. 3,993,076 to Fogarty, et al. discloses a device whereby a vessel is occluded by using a resilient tape to press a vessel against a resilient pad. However, this device suffers from the disadvantage that it slips easily. For example, the pulsations of an occluded artery can tend to force the device off of its clamped position on the occluded artery. Conventional surgical clamps have also been adapted to include jaw surfaces containing resilient members or pads. These devices likewise are prone to slipping off of the clamped vessel. This can be especially problematic in situations where, due to obstructions, a vessel has been clamped with only the distal tips of the clamp jaws. In such situations, the vessel can be especially prone to slipping in the direction of the distal tips.

Other attempts have been made to atraumatically occlude a vessel in a more secure fashion. U.S. Pat. No. 3,746,002 to Haller discloses a vascular clamp with resilient gripping members located on the jaws. A plurality of pin members are embedded within the gripping members, the pin members being of a length such that when a vessel is clamped between the members, the resilient material deflects to accommodate the vessel, exposing the pin members which grippingly engage the outer layer of the vessel, thus securing the vessel to the gripping member. While the Haller device is less traumatic to a vessel than other occlusion devices, it nevertheless has the disadvantage of traumatizing the outer layer of the vessel.

U.S. Pat. No. 4,821,719 to Fogarty discloses a vascular clamp device containing resilient pads with Velcro-like hooks. The hooks interact with the external adventitial layer of the vessel forming a cohesive-adhesive relationship with the vessel similar to the bonding of Velcro materials. While this device offers a less traumatic way to occlude a vessel, the cohesive-adhesive nature of the bond can result in the removal of some of the adventitial layer of the vessel when disengaging the device.

U.S. Pat. No. 3,515,139 to Mallina discloses surgical forceps with hard plastic inserts having spherical protuberances and complementary grooves or spherical cavities. U.S. Pat. No. 3,503,397 to Fogarty discloses surgical clamps with jaw inserts having hard plastic teeth along the edges of the insert with a softer component along the interior of the insert. The hard teeth of this device serve to resist movement of a clamped vessel laterally of the jaw, but do so at increased risk of trauma to the vessel.

There is thus a need for a surgical clamp which atraumatically occludes vessels with improved gripping capabilities while simultaneously avoiding the disadvantages previously associated with existing surgical clamps or occlusion devices.

SUMMARY OF THE INVENTION

The present invention provides for opposing surgical clamp members having opposing resilient pads with clamping surfaces that have interdigitating protrusions or "teeth" that extend from the surfaces of the pads for engagement with a vessel. As used herein, the general term "vessel" shall refer to a blood vessel or other tubular body structure. The protrusions are arranged in rows lengthwise along pairs of opposable pads such that when the pads are brought together, the protrusions of one pad interdigitate with the protrusions of the other pad. When engaged with a vessel, portions of the vessel, including the adventitial layer, will be forced into the interdigital spaces between the protrusions, providing for improved gripping of the vessel or tissue. At the same time, the resiliency of the protrusions ensures against trauma to the clamped vessel or tissue.

The protrusions themselves can be of varying shapes, including cylindrical-shaped protrusions or wedge-shaped protrusions. Where cylindrical protrusions are used, the protrusions can culminate in varying tip shapes, for example, blunt cut, hemispherical or conical tips can be used. The protrusions can also include discrete gripping edges to further increase the traction on an engaged vessel. In every case, the resiliency of the protrusions is such that the protrusions will deflect upon engagement with a vessel but will not distort too greatly from their overall original shape. It is important that the resiliency of the pad as a whole is adequate to impart a cushioning effect upon the clamped vessel, while at the same time the protrusions of the pad retain enough of their original shape to effectively interdigitate with the protrusions of the opposing pad when the pads are brought together in engagement with the vessel. In this manner, the engaged vessel is effectively gripped while minimizing trauma or damage to the vessel. Optimally, the pad itself is of a single-piece construction with the protrusions integrally formed with the remainder of the pad.

In an embodiment of the invention, the relative resiliency of the pad can be altered by including a series of through holes located below the pad surface and transverse to the length of the pad. The holes can be of varying diameter and varying spacing. One skilled in the art will realize that multiple arrangements of through holes can be used, provided that the result is that the underlying portion of the pad containing the through holes is more easily deflected than the protrusions of the overlying surface portion of the pad. The pad thus provides a greater overall cushioning effect for a clamped vessel while at the same time providing the gripping protrusions with a sufficient hardness to resist excessive deformation upon engagement with a clamped vessel. The through holes can extend along the entire length of the pad or, alternatively, extend only along the portions of pad length, for example, along the center portion of the pad. In this latter configuration, the pad will be more easily deflected along the center portion and stiffer towards the ends of the pad. Vessels clamped in the center of the pads will be restrained from slipping toward the ends of the pads because movement of the vessel in those directions will be resisted in part due to the stiffer resilience of the end portions of the pads.

In further embodiments of the invention, the protrusions can be oriented to further resist movement of clamped vessel in particular directions relative to the pads. In one embodiment, the protrusions can be formed in the shape of wedges oriented perpendicular to the length of the pad with the raised ends of the wedges flush with the sides of the pad. In this configuration, movement of a clamped vessel in a direction transverse to the pad will be restricted by the raised ends of the wedges. By arranging the wedges in alternating fashion along the pad length, lateral or transverse movement of a clamped vessel relative to the pad is restricted. In other embodiments, the protrusions can be cylindrical and extend upward from the pad surface. In such configurations, lateral or transverse movement of the clamped vessel relative to the pad will be restricted in like fashion.

BRIEF DESCRIPTION OF THE DRAWINGS

FIG. 3 is a perspective view of opposing surgical clamping members capable of attachment to the jaws of a surgical clamp, with opposing surfaces having protrusions according to a first embodiment of the present invention;

FIG. 4 is a plan view of one of the clamping members of FIG. 3;

FIG. 5 is an end view of the clamping member of FIG. 4;

FIG. 6 is a side view of the clamping members of FIG. 3 with the opposing surfaces of the members aligned with each other;

FIG. 7 is a cross-sectional view of the members of FIG. 6 taken on the plane designated by line 7—7 of FIG. 6;

FIG. 8 is a side view of a clamping member similar to the clamping members of FIG. 6;

FIG. 9 is an end view of the clamping member of FIG. 8;

FIG. 10 is a perspective view of opposing surgical clamping members according to a second embodiment of the present invention with opposing surfaces having a different arrangement of protrusions;

FIG. 11 is a plan view of one of the clamping members of FIG. 10;

FIG. 12 is an end view of the clamping member of FIG. 11;

FIG. 13 is a side view of the clamping members of FIG. 10 with the opposing surfaces of the members aligned with each other;

FIG. 14 is a cross-sectional view of the members of FIG. 13 taken on the plane designated by line 14—14 of FIG. 13;

FIG. 15 is a perspective view of opposing surgical clamping members according to a third embodiment of the present invention with opposing surfaces having another arrangement of protrusions;

FIG. 16 is a plan view of one of the clamping members of FIG.15;

FIG. 17 is an end view of the clamping member of FIG. 16;

FIG. 18 is a side view of the clamping members of FIG. 15 with the opposing surfaces of the members aligned with each other;

FIG. 19 is a cross-sectional view of the members of FIG. 18 taken on the plane designated by line 19—19 of FIG. 18;

FIG. 20 is a side view of a surgical clip with attached clamping members according to a fourth embodiment of the present invention;

FIG. 21 is a perspective view of opposing surgical clamping members according to the fourth embodiment of the present invention, illustrating the arrangement of the protrusions on the opposing surfaces and that the clamping members are capable of attachment to the jaws of a surgical clip;

FIG. 22 is a plan view of one of the clamping members of FIG. 21;

FIG. 23 is a side view of the clamping member of FIG. 22;

FIG. 24 is an end view of the clamping member of FIG. 23;

FIG. 25 is an end view of the jaws of the spring clip depicted in FIG. 20 with attached clamping members according to the present invention; and FIG. 26 is a cross-sectional view of the jaw-clamping member assembly of FIG. 20 taken on the plane designated by line 26—26 of FIG. 20.

DETAILED DESCRIPTION OF THE INVENTION

Figure 1:
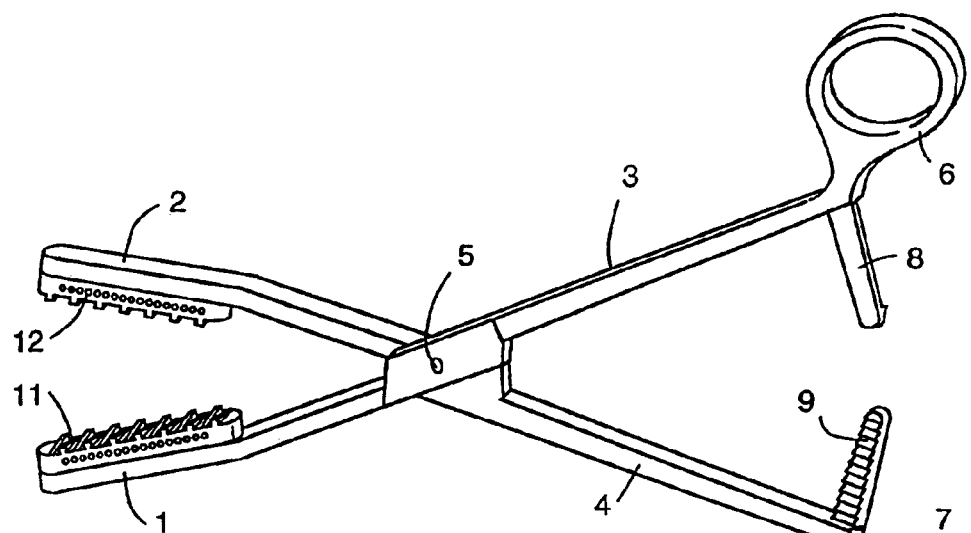
FIG. 1 is a perspective view of a surgical clamp with attached clamping member according to the present invention.
Figure 2:
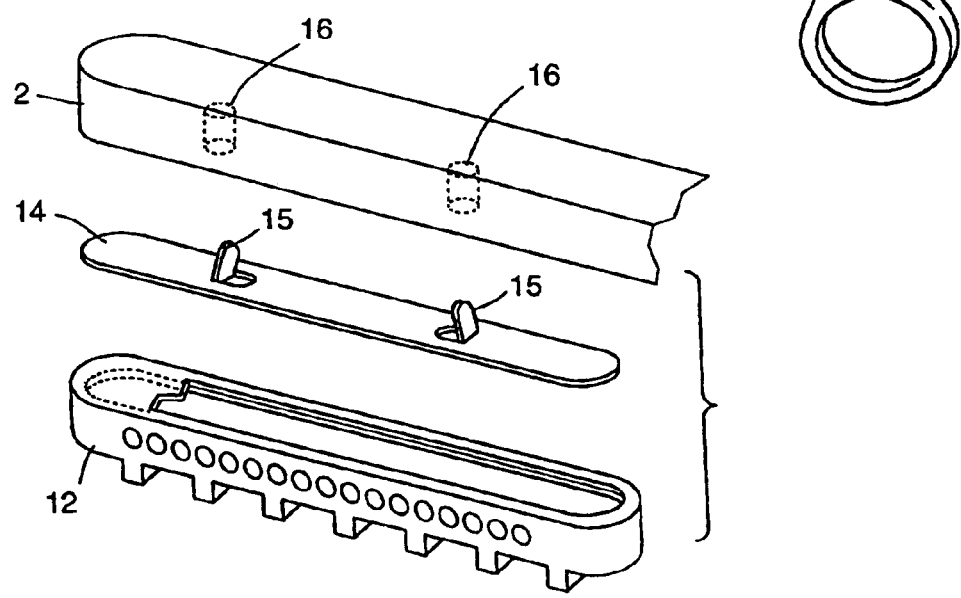
FIG. 2 is an exploded perspective view of the surgical clamp of FIG. 1 with part of the clamp broken away.

FIG. 1 illustrates a surgical clamp comprising a pair of opposed jaws 1 and 2 and handles 3 and 4 hinged together by pin 5. The handles 3 and 4 terminate in finger and thumb rings 6 and 7 which provide for manual operation of the jaws by a surgeon. Interlocking pawl 8 and ratchet teeth 9 are provided on handles 3 and 4, respectively, to secure jaws 1 and 2 in an adjusted clamped position. The opposed jaws 1 and 2 include clamping members according to the present invention comprising opposed pads 11 and 12. The pads themselves are secured to base members 14 that are in turn detachably secured to opposed jaws 1 and 2. As depicted in FIG. 2, base member 14 provides a rigid backing for pad 12 as well as means for attachment of pad 12 to opposed jaw 2. Base members can be made of metal, such as stainless steel, or of a hard plastic, such as polycarbonate. As shown in FIG. 2, a means for attaching pad 12 to opposed jaw 2 can comprise a pair of tabs 15, 15 on base member 14 that can be detachably secured to corresponding recesses 16, 16 on jaw 2.

The pads are comprised of a resilient material having raised protrusions extending from the surfaces of the pads, and it is preferred that the pads are of a single piece construction where the protrusions are integrally formed with the remainder of the pad. The resilient material can have a resilience ranging from about 30 to about 60 durometer. A variety of resilient materials are useful for forming the pads, including natural rubber, neoprene, urethane, ethyl vinyl acetate foam or silicone foam. The preferred resilient material is silicone rubber or silicone. The preferred method of making the pads is to liquid injection mold the pads using silicone, according to ways known in the art.

The invention contemplates various sizes, shapes and arrangements of protrusions, as exemplified by the various embodiments. In all cases the protrusions are of a size, shape and arrangement so that the protrusions of opposing pads interdigitate with one another when the opposing pads are moved toward one another. By interdigitate it is meant that the protrusions of one pad extend into spaces between counterpart protrusions of the other pad when the pads are moved towards one another. Once brought together, remaining or interdigital spaces will exist between the now interdigitated protrusions of the pads. Vessels engaged between the pads, including the advential layer of such vessels, will be forced under clamping pressure to wind around the protrusions and into the interdigital spaces. The displacement of the clamped vessel into the interdigital spaces increases the traction and gripping force of the pads upon the engaged vessel or tissue and increases the force required to move the gripped vessel or tissue relative to the pads. In addition, protrusions having gripping edges provide additional traction and further resist movement of the gripped vessel in directions transverse to the gripping edges.

One skilled in the art will recognize that a number of different shapes, sizes and arrangements of interdigitating protrusions can be used in the present invention and the invention is not intended to be limited to the specific embodiments that follow.

First Embodiment

A first embodiment of a clamping member according to the present invention is depicted in FIGS. 3–9. Resilient pads 31 and 32 are attached to base members 33 and 34, respectively. Pads 31 and 32 are comprised of silicone and formed around base members 33 and 34 by a conventional liquid injection-molding process well known in the art. Once the pads cure or harden, the base members are permanently secured to the pads. Base members 33 and 34 are formed of stainless steel and include spaced apart tabs 35, 35 that can be detachably secured within corresponding recesses in the jaw of a surgical clamp. The tabs are slightly angled toward each other and the respective recesses are undercut so that once the tabs are placed within the recesses, the ends of the tabs snap beneath the undercut, releasably securing the pad to the jaw.

Protrusions in the general shape of wedges 30 extend from planar surface 36 of each pad 31, 32. The wedges are arranged in rows along the length of each pad and each wedge is oriented transverse to the length of the pad. The wedges of the first row are staggered relative to the wedges 30 of the second row, that is, the wedges of the first row and second row alternate, as shown in FIG. 3. In the preferred embodiment, the upright ends of the wedges of the first row are formed flush with the side 37 of the pad 31, and the inclined surfaces of the wedges slope downward and terminate at the side 38, along the same line of intersection as the planar surface 36 and side 38. The wedges of the second row are arranged conversely, with the ends flush with side 38 and the inclined surfaces sloping downward to terminate along the line of intersection between planar surface 36 and side 37.

In operation, when the two pads are brought together, the wedges of one pad interdigitate with the wedges of the other pad and the inclined surfaces of the wedges of one pad mate with the inclined surfaces of the corresponding wedges of the opposed pad, as depicted in FIGS. 6–7. The gripping edges of the wedges provide for improved traction in gripping a clamped vessel. The sides of the wedges resist relative movement of the clamped vessel engaged between the two pads along a direction parallel to the length of the pad. The raised ends of the wedges resist relative movement of the clamped vessel in a direction transverse to the length of the pad. By alternating the orientation of the wedges along the pad, lateral movement can be restricted in either direction transverse to the length of the pad.

The wedges can have a height to width to length ratio ranging from about 1:1:2.5 to about 1:1:4 with the length of the wedge being generally equal to the overall pad width. Wedges of these dimensions that have the appropriate resiliency will retain their shape upon engagement with a vessel. Wedges that are too thin relative to their height will have a tendency to bend over upon themselves upon engagement with a vessel. In such a case, the gripping edges of such wedges will not contact the vessel and the effective interdigitation of opposing wedges will be thwarted.

Most vessels subject to clamping by the pads of the present invention will have diameters ranging from 0.10 to 3.0 inches, with the diameter of the average vessel being about 0.25 inches. For best gripping, it is desirable that several wedges of a pad are in contact with a clamped vessel at any one time. Preferably, the wedges have a width of approximately 0.030 to 0.080 inches, a height of approximately 0.024 to 0.080 inches, and a length equivalent to the pad width, that is, about 0.125 inches. In the preferred embodiment, the wedges are 0.040 inches high, 0.040 inches wide and 0.125 inches in length. Gaps between the wedges are also provided for in this embodiment of the invention, as depicted in FIGS. 3–7. The preferred gap width is 0 to 0.16 inches, and is most preferably 0.040 inches. A vessel clamped between pads of this configuration will have portions of the vessel engaged between the inclined surface of opposing reciprocal wedges alternating with portions engaged in the gap areas between the wedges. The result is alternating areas of high compression and low compression along the clamped vessel. The transition areas between the areas of high and low compression provide for an additional source of traction for gripping the vessel.

As shown in FIGS. 3–7, the relative resiliency of pads 31, 32 are adjusted by the inclusion of a series of through holes 39 passing through each pad below each pad surface. The holes can occur along the entire length of the pad or along a discrete portion of the pad. The holes can be uniform or varying in diameter, and can be equally or variably spaced along the pad length. Preferably, the holes are uniform in diameter, uniformly spaced, and are oriented with the axis of each hole transverse to the pad length. In the most preferred embodiment, the holes are 0.040 inches in diameter, are spaced 0.060 inches apart as measured from the centers of each hole. The holes run along the entire length of the pad, with the exception of the terminal end portions of the pad, corresponding to about 5–10% of the total pad length, as shown in FIG. 6. In the preferred embodiment, the pad itself is formed of a 50 durometer silicone (GE 6050) but the inclusion of the through holes yields a pad with an effective resilience of 35 durometer, as measured by an "A" scale durometer tester (VWR Scientific, Westchester, Pa.). The provision of the through holes in the pad reduces the overall relative resiliency of the pad thereby providing for a greater cushioning effect on a clamped vessel. At the same time this overall reduction in resiliency allows for the wedges 30 themselves to have a stiffer resiliency so they can better retain their general shape and gripping edges upon engagement with a clamped vessel and more effectively interdigitate with wedges of opposing pads, providing for improved gripping of the clamped vessel.

FIGS. 8–9 depict a variation of the first embodiment with a pad configuration similar to that shown in FIGS. 3–6. In this variation the pad 41 has through holes 49 of a larger diameter than those depicted in FIGS. 3–7. The through holes are approximately 0.060 inches in diameter and are spaced apart at a distance of approximately 0.080 inches, relative to the centers of each hole. As depicted in FIGS. 8–9, the through holes span only the center portion of pad 41, corresponding to about 70% of the total pad length. With this configuration of through holes, the pad has a softer overall resiliency along the center portion of the pad than at either end of the pad. A pad of this configuration comprised of 50 durometer silicone will have an effective resiliency of approximately 30 durometer along the center portion of the pad containing the through holes, while the resiliency of the pad at either end will remain at approximately 50 durometer. The relative hardness of the ends of the pads as compared to the center portion helps to resist movement of a vessel clamped in the center of the pads toward either ends of the pads.

In addition, pad 41 includes ridge 42 running lengthwise along the bottom surface of the pad. Base member 43 contains a corresponding depression to receive ridge 42, and the pad is secured to the base member, preferably with an adhesive. The base member itself is formed of a hard plastic, such as polycarbonate. The base member also includes spaced apart knobs 45 that are received into reciprocal recesses in a jaw member of a surgical clamp to releasably secure the clamping member to the jaw member. The recesses are undercut and the heads of the knobs have slight protrusions directed toward one another that snap into the undercut of the recesses to secure the pad to the jaw member.

Second Embodiment

A second embodiment of a clamping member according to the present invention is depicted in FIGS. 10–14. Resilient pads 61 and 62 are attached to base members 63 and 64, respectively. Preferably, the pads 61 and 62 are of 50 durometer silicone (GE 6050) and are formed around base members 63 and 64 in similar fashion as described above for the first embodiment. Again, base members 63 and 64 are formed of stainless steel, and include tabs 65, 65 that can be detachably coupled to corresponding recesses in the jaw of a surgical clamp. Cylindrical protrusions 60 extend from planar surface 66 of each pad 61, 62. The protrusions 60 are arranged in two rows along the length of each pad 61, 62 with the protrusions of the first row staggered relative to the protrusions of the second row, as depicted in FIG. 11. As shown in FIG. 12, the cylindrical protrusions 60 extend from the pad surface 66 perpendicular to the pad surface and can terminate in hemi-spherical tips. The protrusions have a height to width ratio ranging from about 0.8:1 to about 1:1. In the preferred embodiment, the protrusions are 0.040 inches high, 0.040 inches wide, and are spaced at intervals of approximately 0.100 inches within each row. The distance between the two rows is approximately 0.060 inches.

In operation, when the two pads are brought together, the protrusions of one pad interdigitate with the protrusions of the opposing pad. The side walls of the protrusions, oriented in at right angles to the pad surface, present barriers to the movement of a clamped vessel engaged between the two pads in any direction parallel to the plane of the pad surface, including directions both parallel and transverse to the pad length.

In this embodiment, as in the first embodiment, the relative resiliency of the pad can be adjusted by providing a series of through holes 69 passing through each pad below each pad surface. Again, the holes can occur along the entire length of the pad or along a discrete portion of the pad. The holes can be of uniform or varying diameter, and can be uniformly or variably spaced along the pad length. Preferably, the holes 69 are uniform in diameter, run the length of the pad, and are oriented with the axis of each hole transverse to the pad length, as depicted in FIGS. 13–14. In the preferred embodiment, the holes are 0.040 inches in diameter and are spaced 0.060 inches apart, relative to the centers of each hole. Again, the provision of the through holes in the pad reduces the overall relative resiliency of the pad thereby providing for a greater cushioning effect on a clamped vessel. At the same time this overall reduction in resiliency allows for the protrusions 60 themselves to have a stiffer resiliency so they can better retain their general shape upon engagement with a clamped vessel and more effectively interdigitate with protrusions of the opposing pad, thereby providing for improved gripping of the clamped vessel. In this embodiment, as in the first embodiment, while the pad is comprised of a 50 durometer silicone, the provision of the through holes provides for an effective pad resiliency of approximately 35 durometer.

Third Embodiment

A third embodiment of a clamping member according to the present invention is depicted in FIGS. 15–19. Resilient pads 71 and 72 are formed of 40 durometer silicone (GE 6040) and attached to base members 73 and 74, respectively, preferably by the use of an adhesive. The base members 73 and 74 are formed of a hard plastic, such as polycarbonate, and include knobs 75, 75 that can be detachably coupled to corresponding recesses in the jaw of a surgical clamp, as described above with respect to the FIG. 8 and 9 variation of the first embodiment. Cylindrical protrusions 70 extend from planar surface 76 of each pad 71 and 72, and are arranged in a single row along the length of each pad, as depicted in FIGS. 15–18. As shown in FIG. 17, the cylindrical protrusions 70 extend from the pad surface 76 in a direction perpendicular to the pad surface. The cylindrical protrusions 70 themselves terminate in conical tips 77. In alternative embodiments, the protrusions can terminate in rounded or flat tips. The protrusions have a height to width ratio ranging from 1:1 to about 1:2. In the preferred embodiment, the cylindrical protrusions have a height of 0.040 inches to the base of the conical tip, with the conical tip extending another 0.010 inches. The protrusions are approximately 0.063 inches wide and are spaced at intervals of approximately 0.100 inches.

In operation, when the two pads are brought together, the protrusions of one pad interdigitate with the protrusions of the opposing pad. The side walls of the protrusions, oriented at right angles to the pad surface, present barriers to the movement of a clamped vessel engaged between the two pads in any direction parallel to the plane of the pad surface, including directions both parallel and transverse to the pad length.

Fourth Embodiment

A fourth embodiment of the clamping member according to the present invention is depicted in FIGS. 20–26. This embodiment is designed to attach to surgical spring clips of the type depicted in FIG. 20. The surgical clip shown in FIG. 20 comprises a pair of opposing jaws 81 and 82 that are attached to cylinders 83 and 84, respectively. Each cylinder has an open end, a closed end, and an interior chamber. Cylinder 84 is of a smaller diameter than cylinder 83 and nests inside cylinder 83. Eyelet 87 extends outward from cylinder 83. Jaw 82 is attached to the outer wall of cylinder 84 at the open end of cylinder 84 and jaw 81 is likewise attached to the outer wall of cylinder 83 at the open end of cylinder 83. Spring 88 extends lengthwise within the interior chambers of the cylinders, with the ends of the spring in engagement with the closed ends of the cylinders. The spring pushes against the closed end of each cylinder to force the cylinders apart, thereby bringing jaws 81 and 82 together. A guide slot 89 is provided in cylinder 83 to allow movement of jaw 82 relative to cylinder 83. To operate the clip, a surgeon manually squeezes the end caps 85 and 86 together against the force of spring 88, thereby moving the cylinders together and simultaneously moving jaws 81 and 82 apart. The clip can then be positioned for engagement with a vessel and the pressure on the end caps released, bringing the jaws together again in a clamped position in engagement with the vessel.

Resilient pads 91 and 92 are comprised of 50 durometer silicone (GE 6050) and attached to jaws 81 and 82 by means of a ridge 95 running lengthwise along the undersides of the pads. These ridges are received into corresponding T-shaped channels 97 and 98 in jaws 81 and 82, respectively, and are secured in place by an adhesive 96, such as silicone RTV (GE 118). The adhesive bonds with the pad to form a T-shaped section that is engaged by T-shaped channels 97, 98. As in the first embodiment, protrusions in the general shape of wedges 90 extend from each pad. The wedges are arranged in rows along the length of each pad and each wedge is oriented transverse to the length of the pad. The wedges of the first row are staggered relative to the wedges of the second row, that is, the wedges of the first row and second row alternate, as shown in FIG. 21. The upright ends of the wedges of the first row are formed flush with one side of the pad, and the inclined surfaces of the wedges slope downward and terminate at the other side of the pad. The wedges of the second row are arranged in reciprocal fashion.

This embodiment of the invention operates in similar fashion to the first embodiment. When the two pads are brought together, the wedges of one pad interdigitate with the wedges of the other pad and the inclined surfaces of the wedges of one pad mate with the inclined surfaces of the corresponding wedges of the opposed pad. The sides and raised ends of the wedges resist relative movement of a clamped vessel engaged between the two pads along directions parallel and transverse to the length of the pad. Unlike the first embodiment, this embodiment does not provide for gaps between the wedges. This embodiment has the advantage of being able to grip vessels of very small diameter that could otherwise slip through the gap spaces of the first embodiment. A surgical clip utilizing the pads of this embodiment can also perform alternative functions, such as use as a surgical "tag" for tagging sutures during surgery to aid a surgeon in identifying and locating sutures during the course of an operation. The wedges formed flush with one another and without intervening gaps provide for improved for gripping of sutures in the same fashion as for small diameter vessels.

The wedges have a height to width to length ratio ranging from about 1:1:2.5 to about 1:1:4 with the length of the wedge being generally equal to the overall pad width. Preferably, the wedges have a width of approximately 0.030 to 0.080 inches, a height of approximately 0.024 to 0.080 inches, and a length equivalent to the pad width, that is, about 0.10 inches. In the preferred embodiment, the wedges are 0.040 inches high, 0.040 inches wide and 0.10 inches in length.

Although only certain embodiments have been illustrated and described, those having ordinary skill in the art will understand that the invention is not intended to be limited to the specifics of these embodiments, but rather is defined by the accompanying claims.

We claim:

1. Surgical clamp members for attachment to opposing surfaces of jaws of a surgical clamping device, the jaws being mounted for movement toward and away from one another, the members comprising:

opposable resilient pads, each pad having a surface, the surface having discrete raised protrusions extending upward therefrom for engagement with a vessel or other tissue received between the jaws, wherein:

a) the protrusions of each pad are arranged in one or more rows lengthwise along the pad; and b) the protrusions of one pad interdigitate with the protrusions of the opposed pad when the jaws are moved toward one another, and wherein each said pad surface is planar and the protrusions extending therefrom are cylindrical and extend from the pad at right angles to the pad surface.

2. The clamp members of claim 1 wherein said protrusions have hemispherical tips.

3. The clamp of claim 1 wherein said cylindrical protrusions have conical tips.

4. The clamp members of claim 1 wherein:

a) said protrusions form first and second rows lengthwise along the pad; and b) the protrusions of the second row are staggered relative to the protrusions of the first row.

5. The clamp member of claim 4 wherein;

a) each pad has first and second sides and one or more cylindrical holes passing through the pad and opening to both first and second sides; and b) each cylindrical hole has an axis transverse to the pad length.

* * * * *